Figure 1:
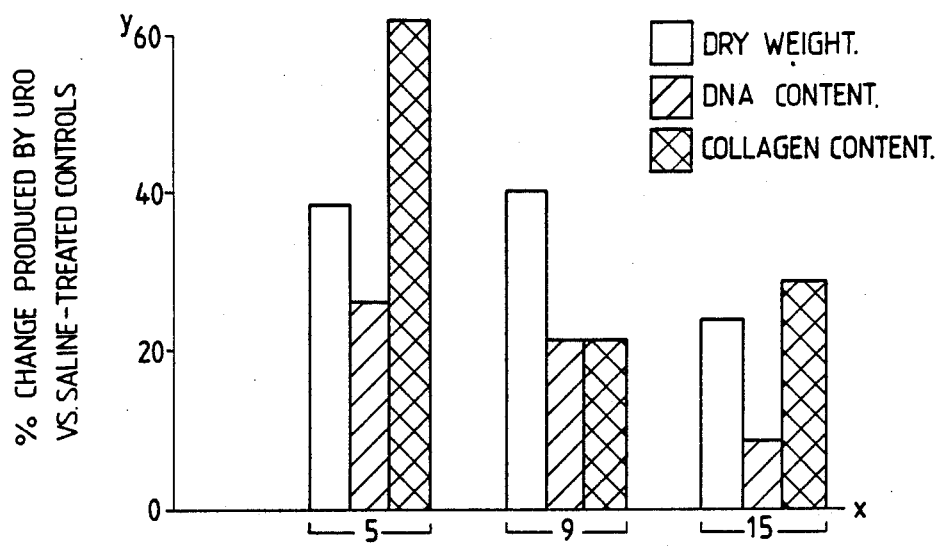

United States Patent [19]

Franklin et al.

[11] Patent Number: 4,731,357
[45] Date of Patent: Mar. 15, 1988

[54] UROGASTRONE

[75] Inventors: Trevor J. Franklin; Harold Gregory; William P. Morris, all of Cheshire, England

[73] Assignee: Imperial Chemical Industries PLC, London, England

[21] Appl. No.: 844,154

[22] Filed: Mar. 26, 1986

[30] Foreign Application Priority Data

Apr. 12, 1985 [GB] United Kingdom ................ 8509448

[51] Int. Cl.$^4$ .............................................. A61K 37/02
[52] U.S. Cl. ........................................ 514/10; 514/12
[58] Field of Search .................................... 514/10, 12

[56] References Cited

FOREIGN PATENT DOCUMENTS 0105014 4/1984 European Pat. Off. .
W84/01106 3/1984 Int'l Pat. Institute .
1394846 5/1975 United Kingdom .

Primary Examiner—Delbert R. Phillips
Attorney, Agent, or Firm—Cushman, Darby & Cushman

[57] ABSTRACT

The use of human urogastrone or a human urogastrone fragment for the manufacture of a medicament for promoting bone and/or tendon repair is described. The medicament is adapted for topical or parenteral administration and is preferably administered directly to the site of the wound or to a site in close proximity thereto.

8 Claims, 4 Drawing Figures

DAYS AFTER SURGERY

UROGASTRONE

The present invention relates to a method of promoting bone and/or tendon repair in man and other warm-blooded animals by the use of urogastrone and the use of urogastrone for the manufacture of a medicament for promoting bone and/or tendon repair.

Urogastrone is a 53-residue single-chain polypeptide of about 6000 daltons having the following structure:

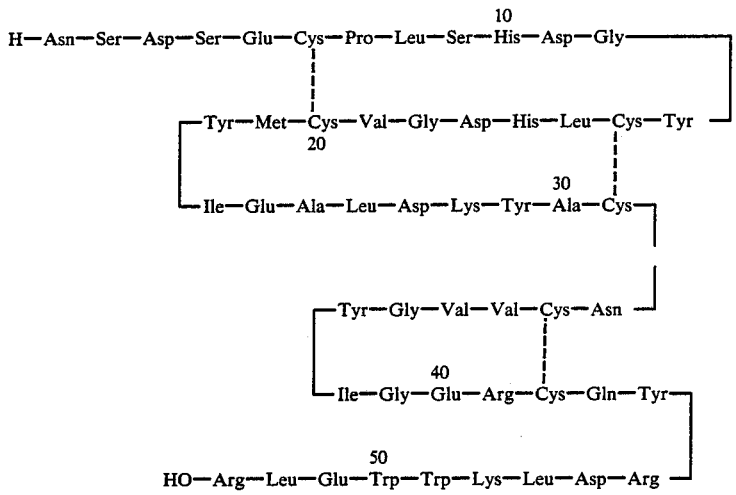

Urogastrone was originally isolated from human urine and is described and claimed in our British Pat. No. 1,394,846. The structure of urogastrone was first elucidated by H. Gregory et al in 1975 [Nature, 257, 325 (1975)].

Urogastrone is known to inhibit acid secretion in the stomach when administered parenterally, but the present invention is based on the discovery that urogastrone will promote bone and/or tendon repair. This is of particular interest since bone and tendons are slow to heal, being poorly vascularized. In spite of the fact that the structure of urogastrone was published as long ago as 1975 there has been no investigation, published in the literature, of the utility of urogastrone in promoting the healing of such wounds and the in vivo tests described hereinafter constitute the first evidence of this utility in tendon repair. Moreover, since urogastrone per se is a natural human product, the potential problems of immunogenicity inherent in material foreign to the human are minimised.

Thus, according to one feature of the present invention there is provided a method of promoting bone and/or tendon repair in a warm-blooded animal which comprises the topical or parenteral administration of an effective amount of human urogastrone or a human urogastrone fragment, as hereinafter defined, to said animal.

According to a further feature of the present invention there is provided the use of human urogastrone or a human urogastrone fragment for the manufacture of a medicament adapted for topical or parenteral administration for promoting bone and/or tendon repair.

According to a still further feature of the present invention there is provided the use of human urogastrone or a human urogastrone fragment as hereinafter defined for promoting bone and/or tendon repair.

According to a still further feature of the present invention there is provided an agent for promoting bone and/or tendon repair which comprises human urogastrone or a human urogastrone fragment as active ingredient.

The present invention is particularly of interest in promoting the healing of bone and/or tendon injuries caused by accident or intent rather than by disease or bodily malfunction, and includes for example tendon grafting.

The term "human urogastrone or a human urogastrone fragment" as used herein preferably refers to the polypeptide hormone described by Gregory H. in Nature, 257, 325–327 (1975). If desired however a urogastrone fragment capable of promoting the healing of the aforesaid wounds may be used. Such a fragment may for example be a polypeptide comprising only amino acids 1-46, 1-47, 1-48, 1-49, 1-50, 1-51 or 1-52. It will be appreciated that references herein to urogastrone or a urogastrone fragment include such polypeptides which carry a methionine or formylmethionine at their N-termini as well as such polypeptides which carry a peptide sequence of up to 12 amino acid residues at their N-termini, which sequence may in turn be preceded by methionine or formylmethionine, providing that the total number of amino acid residues preceding the N-terminus does not exceed 12.

The present invention is applicable to non human warm-blooded animals for example domestic animals, such as cats and dogs, and farm animals, such as cattle, and horses as well as to humans.

The human urogastrone or urogastrone fragment as herein defined is preferably administered parenterally for example systemically or to the site of the wound or in close proximity thereto. If desired the human urogastrone or urogastrone fragment might also be administered by slow release implant. Where the human urogastrone or human urogastrone fragment is applied topically this will generally be to the site of the wound during surgery.

The present invention is of particular interest in relation to the promotion of tendon repair in humans and other warm-blooded animals such as domestic pets, for example cats and dogs, as well as horses in which urogastrone promotes recovery from equine tendonitis for example resulting from tendon tearing. The use of urogastrone in tendon repair is particularly advantageous in view of the way in which healing is promoted. The use of urogastrone increases differentiation, assists the gliding function of the tendon and promotes regeneration of the original architecture of the tendon and the surrounding tissue. The utility of urogastrone in promoting tendon repair is illustrated by the tests described hereinafter in which the healing of the Achilles tendons of rats is promoted by the use of urogastrone. In these tests the effect of the urogastrone was most pronounced during the first five days after surgery, the enhancement of the collagen content of the urogastrone treated lesions compared with saline-treated controls being particularly marked. The DNA content of the control and urogastrone-treated lesions were both at their maximum nine days after surgery while the enhancing effect of urogastrone on this parameter virtually disappeared by fifteen days. Animals maintained for thirty days on urogastrone treatment revealed a further increase in the collagen content of the lesions although the dry weight and DNA content declined after fifteen days of treatment. The tests suggest that despite continued urogastrone treatment the stimulatory effect of the growth factor on the cellular content of the repair lesion was transient whilst the increase in the collagen content was maintained. Cessation of urogastrone treatment resulted in a decline of the lesion parameters back towards control values. Thus the dry weight and cellularity (as measured by the DNA content) of the proliferating scar tissue peaked in the urogastrone treated tissues and controls at 9 days whereas the collagen synthesis continued to increase over 15 days in both treated and control tendons thus showing that the scar appears to mature in a natural way.

The method of the present invention is preferably effected by the parenteral or topical administration of human urogastrone or a human urogastrone fragment or a pharmaceutical or veterinary compositon comprising human urogastrone or a human urogastrone fragment as active ingredient in association with a physiologically compatible carrier or excipient.

Urogastrone may be formulated into a pharmaceutical or veterinary composition by any convenient technique. Urogastrone is conveniently the sole growth factor present in the composition. The compositions may be presented in a form suitable for parenteral administration, for example in ampoules or vials. Thus for patenteral administration the human urogastrone or human urogastrone fragment as defined herein is preferably formulated as an isotonic solution, for example in dextrose or physiological saline. Where the human urogastrone or human urogastrone fragment is applied topically to the site of the wound during surgery the composition employed may be formulated in any suitable carrier such as physiological saline solution. The compositions for use in the present invention may if desired comprise adjuvants such as for example antiseptic or antimicrobial agents.

Where the composition is presented in a form suitable for parenteral administration it may be presented in dosage unit form each dosage unit preferably containing from 1 μg. to 10 mg., especially 25 μg. to 1 mg. of human urogastrone or urogastrone fragment.

As stated above the preferred method of administration is direct to the site of the wound or injury or in close proximity thereto. It may be preferred in relation to parenteral administration to deliver the parenteral formulation to a site sufficiently close to the wound to allow the human urogastrone fragment to pass into the site of the wound whilst not delivering the human urogastrone or fragment directly to the site of the wound per se. Periodic or continued administration may prove advantageous since the urogastrone is employed by the cells whose growth is being promoted. Where such administration is effected topically each subject whether human or other warm-blooded animal will normally receive a dose of urogastrone of from 0.1 to 100 μg./kg. A preferred dose range is from 1 to 100 μg./kg. Where such administration is effected parenterally each subject whether human or other warm-blooded animal will normally receive a dose of urogastrone of from 0.1 to 100 μg./kg./day. A preferred dose range is from 1 to 100 μg./kg./day. The composition may for example be administered 1-4 times daily, preferably once or twice daily.

The pharmaceutical or veterinary composition comprising urogastrone as active ingredient is conveniently associated with written or printed instructions for the use of the composition or medicament for promoting bone and/or tendon repair. The instructions will, for example, state the dosage, the most advantageous method of administration and any conditions in which use of the composition may be contraindicated.

The present invention is exemplified by the promotion of healing which resulted following administration of recombinant urogastrone to rats after the simple transection of their Achilles tendons.

The results given in Table 1 and FIG. 1 hereinafter indicate that during the first five days following surgery urogastrone given near the site of the surgical lesion markedly increased the dry weight of the scar tissue and both its DNA and collagen contents compared with saline-injected controls. Collagen was increased by 61%, DNA by 20% and dry weight by 38%, all these increases being statistically highly significant. At fifteen days after surgery the cumulative effect of urogastrone was less marked, the increases in dry weight and collagen over saline-injected controls being down to 24% and 28% respectively. The apparent increase in the DNA content of urogastrone-treated lesions at day 15 (8%) was not significantly different from the control value. When urogastrone was injected twice daily close to the unoperated tendon in the opposite leg there was little or no effect throughout the treatment period with the possible exception of an increased DNA content after nine days of treatment. In a second experiment the period of twice-daily treatments with urogastrone was extended to thirty days after surgery. Another group of animals was treated for fifteen days only after surgery and then left without further urogastrone treatment until sacrifice fifteen days later. The results in Table 2 and FIG. 2 show that in animals maintained for thirty days on urogastrone the dry weight and collagen content of the repair lesion were respectively 19% and 27% higher than the corresponding values in the saline-treated control lesions. The DNA contents of urogastrone and saline-treated lesions were essentially the same. The increases in lesion values observed after fifteen days treatment with urogastrone were similar to those of the first experiment. When dosing with urogastrone was stopped after fifteen days and the animals kept treatment free for a further fifteen days we found that the dry weight and collagen content of the scars were no longer distinguishable from those of animals untreated throughout the course of the experiment.

Figure 2:
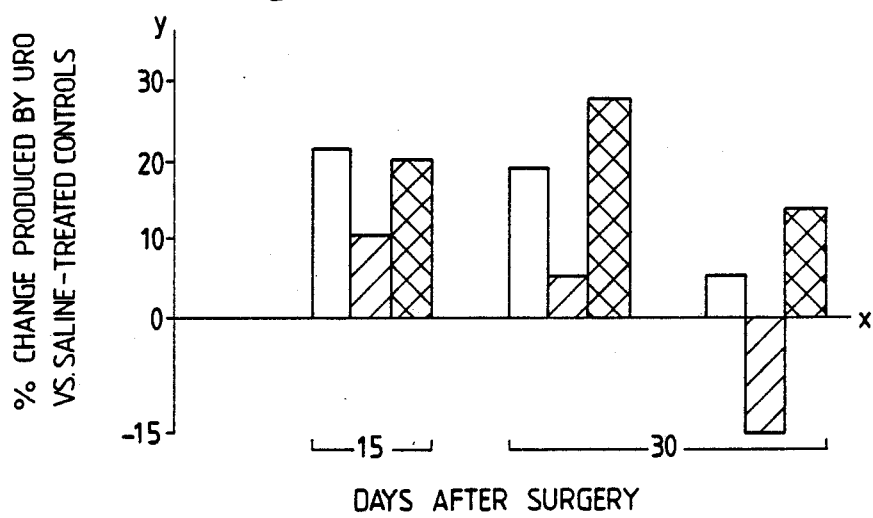

In the drawings attached hereto:

FIG. 1 represents graphically the effects of recombinant urogastrone on the healing of tendon lesions, the data therefor being present in Table 1, and being expressed as percentage increases over saline-treated controls (axis Y) against days after surgery (axis X). Thus FIG. 1 presents graphically the percentage increase of D over C for each of the measured parameters detailed in Table 1 for 5, 9 and 15 days after surgery.

FIG. 2 represents graphically the longer term effects of recombinant urogastrone on the healing of tendon lesions, the data therefor being present in Table 2 and being expressed as percentage increases over saline-treated controls (axis Y) against days after surgery (axis X). Thus FIG. 2 presents graphically the percentage increase of C over B for each of the measured parameters detailed in Table 2 for day 15 after surgery and the percentage increase of D over B for each of the measured parameters detailed in Table 2 for day 30 after surgery. In FIGS. 1 and 2 the differently marked columns have the following meanings:

☐ Dry weight

 DNA content

 Collagen content

Figure 3:
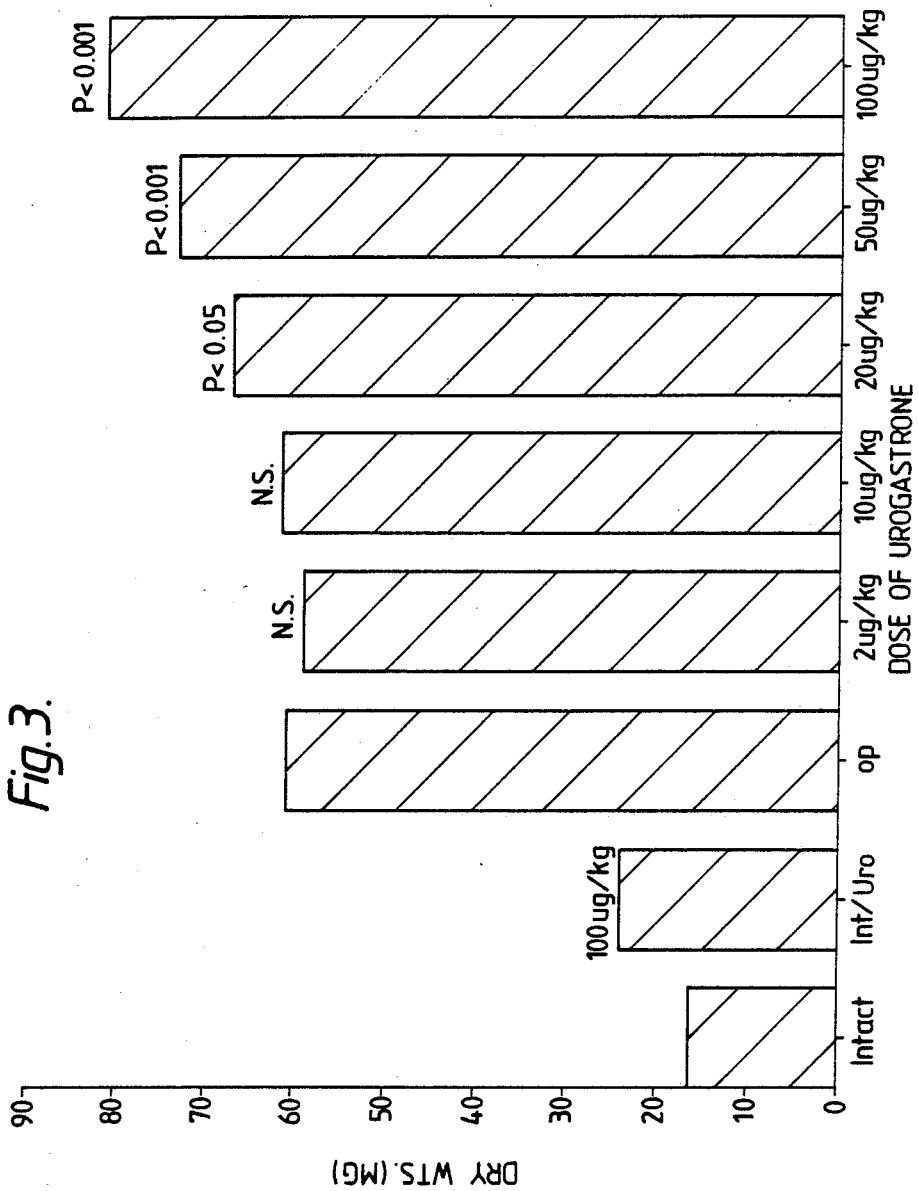

FIG. 3 represents graphically the effect of graded doses of recombinant urogastrone on the healing of sectioned Achilles tendons in rats as measured by the dry weight of the scar tissue formed at the injected zone 15 days after surgery. The graded doses were injected twice daily into the immediate vicinity of the sectioned tendon. FIG. 3 also shows (a) the corresponding dry weights in an intact and operated leg to which no urogastrone was administered, and (b) the corresponding dry weight in respect of intact tendons in to which urogastrone was injected in unoperated rats which received a dose of 100 μg./kg. of urogasteone injected twice daily in the corresponding position in the intact tendon.

Figure 4:
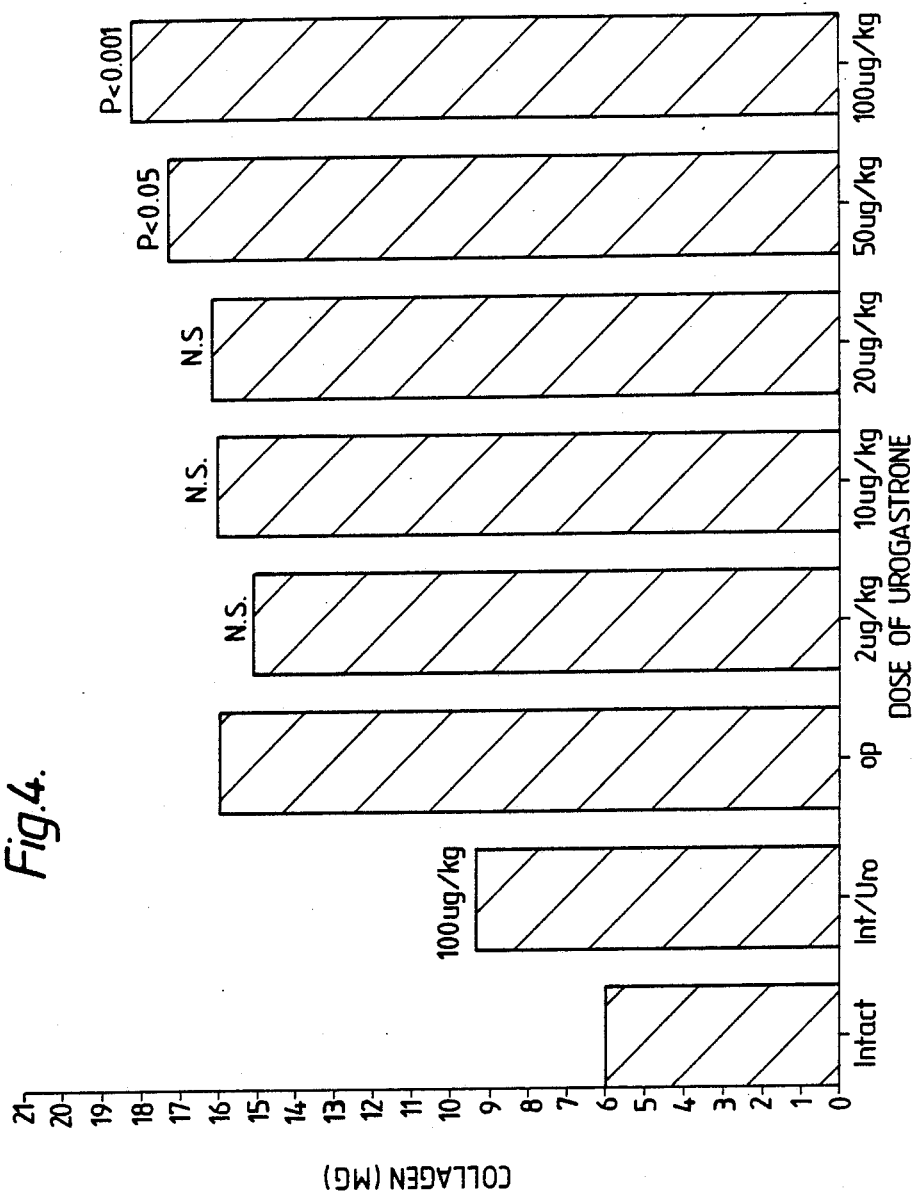

FIG. 4 corresponds to FIG. 3, but represents graphically the collagen content of the repair lesions at the injected zone 15 days after surgery rather than the dry weight of the scar tissue formed at the said zone 15 days after surgery.

EXAMPLE 1

Male Wistar rats (240 g.) were subjected under general anaesthesia to partial tendonotomy of the left Achilles tendon, the small skin wound was then sutured and the animals allowed to recover. Recombinant human urogastrone bearing a 14 amino acid N-terminal leader sequence and an additional Arg oligopeptide at the C-terminus was isolated from E coli, having been prepared as described and claimed in European Patent Application No. 81303517.7 of G. D. Searle & Co. Skokie, Ill., U.S.A. It was converted to the normal 53 amino acid chain by controlled tryptic hydrolysis (15 min at 37°, enzyme-substrate ratio: 1 to 1000) and purification by CM cellulose and Biogel P-6 chromatography. The purified growth factor (urogastrone purity >98%) was dissolved in normal saline and injected twice daily (20 μg./kg. body weight, 5.0 μl.) at the site of the tendon lesion for the indicated number of days after surgery. In experiment 1 (Table 1) urogastrone was also injected at the same dose level and frequency into the corresponding region of the unoperated leg (group [B]), to determine if the same dosing schedule had any effect on the normal tendon. Normal saline was injected into a control group of operated animals (group [C]). In experiment 2 (Table 2) group [D]received urogastrone (20 ug./kg.) twice daily for 30 days while group [C]received urogastrone for 15 days followed by 15 days without treatment. After termination the scar tissue was removed from the point of insertion into the calcaneus bone to the point of merger of the tendon into the muscle mass. Weights of the scar tissue were measured after drying and defatting as described in Greenwald, S. E. and Berry, C. L. Cardiovasc. Res. 12,364–372 (1978). The collagen content was obtained from hydroxyproline measurements as described in Grant, R. A. J. Clin. Path. 17, 685–686 (1964) on the tissue after proteolytic (see Smith, R. L., Gilberson, E., Koliatsu, N., Merchant, T. and Schurman, D. J. Analyst. Biochem. 103, 191–200 (1980)) and alkaline (see Huzar, G., Maiocco, J. and Naftolin, F. Analyt. Biochem. 105 424–439 (1980)) digestion. The DNA content of the digests was determined using a sensitive fluorimetric technique (as described in Hinegardner, R. T. Analyt. Biochem. 39, 197–201). The results are ±SEM and were analyzed by Student's t test. Figures in parentheses indicate the numbers of animals used in each group.

EXAMPLE 2

This Example illustrates the effects of graded doses of urogastrone on tendon healing. The rats employed were male Wistar rats (240 g) and the Achilles tendons were sectioned as described in Example 1. The purified urogastrone used was obtained as in Example 1 and the dry weight and collagen content were measured as described in that Example.

Graded doses of urogastrone were given twice daily by injection into the immediate vicinity of the sectioned Achilles tendon in rats. A dose of 100 ug. of urogastrone/kg. was injected twice daily into the corresponding position in intact tendons in unoperated rats. FIGS. 3 and 4 present the dry weights and collagen contents respectively of the injected zones 15 days after surgery. Doses of 20 μg./kg. produced a statistically significant increase in the dry weights of the repair lesions but not in the collagen contents. Doses of 50 and 100 μg./kg. significantly increased both dry weights and collagen contents. The highest dose also increased the dry weight and collagen contents.

TABLE 1

Effect of daily injections of recombinant urogastrone on healing of sectioned Achilles tendons in the rat when injected into the immediate vicinity of the tendon lesion.

| | Days after surgery | | | | | | | | |
|---|---|---|---|---|---|---|---|---|---|
| | 5 | | | 9 | | | 15 | | |
| Treatment | Lesion dry wt (mg) | DNA (ug) | Collagen (mg) | Lesion dry wt (mg) | DNA (ug) | Collagen (mg) | Lesion dry wt (mg) | DNA (ug) | Collagen (mg) |
| Intact tendon (10) [A] | 10.8±0.6 | 85.4±3.9 | 6.0±0.3 | 13.2±1.2 | 99.5±9.5 | 5.9±0.3 | 12.6±0.7 | 96.8±5.1 | 6.3±0.2 |
| Intact tendon (10) [B] plus urogastrone | 12.7±1.6 | 94.3±8.5 | 6.1±0.3 | 14.1±1.2 | 124±10 | 7.0±0.5 | 11.6±1.0 | 101±6 | 7.0±0.3 |

TABLE 1-continued

Effect of daily injections of recombinant urogastrone on healing of sectioned Achilles tendons in the rat when injected into the immediate vicinity of the tendon lesion.

| | Days after surgery | | | | | | | | |
|---|---|---|---|---|---|---|---|---|---|
| | 5 | | | 9 | | | 15 | | |
| Treatment | Lesion dry wt (mg) | DNA (ug) | Collagen (mg) | Lesion dry wt (mg) | DNA (ug) | Collagen (mg) | Lesion dry wt (mg) | DNA (ug) | Collagen (mg) |
| [A] vs [B] | NS | NS | NS | NS | $p < 0.05$ | NS | NS | NS | NS |
| Sectioned tendon (10) [C] plus saline | 31.0±1.8 | 409±12 | 7.2±0.5 | 43.6±3.0 | 538±20 | 13.8±0.8 | 42.91±2.5 | 514±2 | 15.6±0.8 |
| Sectioned tendon (10) [D] plus urogastrone | 42.9±2.0 | 517±12 | 11.6±0.5 | 61.1±2.0 | 653±20 | 16.8±0.9 | 53.3±2.8 | 556±23 | 20.0±0.8 |
| [C] vs [D] | $p < 0.001$ | $p < 0.001$ | $p < 0.001$ | $p < 0.001$ | $p < 0.001$ | $p < 0.05$ | $p < 0.001$ | NS | $p < 0.001$ |

TABLE 2

Longer term effects of daily injections of recombinant urogastrone on healing of Achilles tendons in the rat on injection into the immediate vicinity of the tendon lesion.

| | Days after surgery | | | | | |
|---|---|---|---|---|---|---|
| | 15 | | | 30 | | |
| Treatment | Lesion dry wt (mg) | DNA (ug) | Collagen (mg) | Lesion dry wt (mg) | DNA (ug) | Collagen (mg) |
| Intact tendon (10) [A] | 12.6 ± 0.5 | 94.4 ± 7.2 | 7.2 ± 0.3 | 15.7 ± 0.8 | 120 ± 15 | 6.9 ± 0.6 |
| Sectioned tendon (10) [B] plus saline | 50.2 ± 1.2 | 604 ± 32 | 23.3 ± 1.2 | 47.8 ± 1.3 | 469 ± 28 | 25.2 ± 1.1 |
| Sectioned tendon (10) [C] plus urogastrone, days 1-15 | 61.8 ± 1.3 | 668 ± 32 | 28.1 ± 0.9 | 50.2 ± 1.1 | 397 ± 17 | 28.7 ± 1.2 |
| [B] vs [C] | $p < 0.001$ | NS | $p < 0.01$ | NS | $p < 0.05$ | NS |
| Sectioned tendon (10) [D] plus urogastrone, days 1-30 | — | — | — | 56.8 ± 2.0 | 495 ± 17 | 32.1 ± 1.3 |
| [B] vs [D] | — | — | — | $p < 0.01$ | NS | $p < 0.001$ |

Formulation Examples

EXAMPLE A

Purified human urogastrone prepared as described in Example 1 is dissolved in pyrogen free 5% w/v dextrose solution to give a final concentration of 40 μg./ml. This solution is dispensed into vials in aliquots of 2.5 ml. each through a sterilising membrane filtration system, for example a 0.22 mμ filter. The contents of each vial are then lyophilised and the vials capped and sealed under sterile conditions. The vials containing a sterile mixture of urogastrone and dextrose are stored at 4° C.

EXAMPLE B

To a vial prepared as described in Example A is added 2.5 ml. of sterile water immediately before use to give a sterile injectable solution of 40 μg./ml. of urogastrone in 5% w/v dextrose solution.

EXAMPLE C

Purified human urogastrone prepared as described in Example 1 was dissolved in pyrogen-free water (50 ml.) and the solution filtered through a sterilising membrane filtration system, for example a 0.22 mμ. filter into ampoules so that each ampoule received 0.5 ml. The contents of each vial were then lyophilised, and the ampoules sealed under sterile conditions. The ampoules, each containing 100 μg. of urogastrone, were kept at −20° C.

EXAMPLE D

The contents of an ampoule prepared as in Example C were dissolved in 5% w/v dextrose solution to give a solution containing 5–50 μg./ml. of urogastrone.

Alternatively the 5% w/v dextrose solution may be replaced by isotonic saline.

We claim:

1. A method of promoting bone and/or tendon repair in a warm blooded animal which comprises the topical or parenteral administration of an effective amount of human urogastrone or a human urogastrone fragment to said animal.

2. A method as claimed in claim 1 wherein the human urogastrone or urogastrone fragment is administered parenterally.

3. A method as claimed in claim 1 wherein the human urogastrone or urogastrone fragment is administered parenterally in a dose of from 0.1 to 100 μg./kg./day.

4. A method as claimed in claim 1 wherein the human urogastrone or urogastrone fragment is administered parenterally in a dose of from 1 to 100 μg./kg./day.

5. A method as claimed in claim 1 wherein the human urogastrone or urogastrone fragment is administered to the site of the wound or to a site sufficiently close to the wound for the dose administered to be effective.

6. A method as claimed in claim 5 wherein the human urogastrone or urogastrone fragment is administered in a dosage of 0.1 to 100 μg./kg.

7. A method as claimed in claim 5 wherein the human urogastrone or urogastrone fragment is administered in a dosage of 1 to 100 μg./kg.

8. A method as claimed in claim 1 wherein the human urogastrone or urogastrone fragment is administered to a horse for treatment of equine tendonitis.

* * * * *